US010993734B2

(12) United States Patent
Sholev et al.

(10) Patent No.: US 10,993,734 B2
(45) Date of Patent: May 4, 2021

(54) CONTROL UNIT FOR A MEDICAL DEVICE

(71) Applicant: Human Extensions Ltd., Netanya (IL)

(72) Inventors: Mordehai Sholev, Moshav Amikam (IL); Liran Elihay, Kiryat Gat (IL); Yuval Blyakhman, Tel-Aviv (IL); Oren Teiblum, Hod-HaSharon (IL); Amit Keren, Zikhron-Yaakov (IL)

(73) Assignee: Hsiman Extensions Ltd., Netanya (IL)

( * ) Notice: Subject to any disclaimer, the term of this patent is extended or adjusted under 35 U.S.C. 154(b) by 206 days.

(21) Appl. No.: 16/081,044

(22) PCT Filed: Mar. 9, 2017

(86) PCT No.: PCT/IL2017/050307
§ 371 (c)(1),
(2) Date: Aug. 30, 2018

(87) PCT Pub. No.: WO2017/154007
PCT Pub. Date: Sep. 14, 2017

(65) Prior Publication Data
US 2019/0069917 A1 Mar. 7, 2019

Related U.S. Application Data

(60) Provisional application No. 62/306,118, filed on Mar. 10, 2016.

(51) Int. Cl.
*A61B 17/29* (2006.01)
*A61B 34/00* (2016.01)
*A61B 17/00* (2006.01)

(52) U.S. Cl.
CPC .......... *A61B 17/2909* (2013.01); *A61B 34/00* (2016.02); *A61B 34/70* (2016.02);
(Continued)

(58) Field of Classification Search
CPC ..... A61B 17/2909; A61B 34/70; A61B 34/74; A61B 2017/003; A61B 2017/00424;
(Continued)

(56) References Cited

U.S. PATENT DOCUMENTS 5,599,151 A * 2/1997 Daum .................. B25J 3/00
294/111
6,676,684 B1 1/2004 Morley et al.
(Continued)

FOREIGN PATENT DOCUMENTS

CN 101594816 12/2009
CN 102665589 9/2012
(Continued)

OTHER PUBLICATIONS

International Preliminary Report on Patentability dated Sep. 20, 2018 From the International Bureau of WIPO Re. Application No. PCT/IL2017/050307. (7 Pages).
(Continued)

*Primary Examiner* — Katrina M Stransky

(57) ABSTRACT

A control unit for a medical instrument is provided. The control unit includes a housing having a curved top surface capable of accommodating a hand of the user, the housing being attachable to the medical instrument. The control unit further includes a first interface engageable by a purlicue of the hand for controlling a first function of the medical instrument and a second interface engageable by one or more fingers of the hand for operating at least a second function of the medical instrument.

21 Claims, 21 Drawing Sheets

(52) U.S. Cl.
CPC ........ *A61B 34/74* (2016.02); *A61B 2017/003* (2013.01); *A61B 2017/0046* (2013.01); *A61B 2017/00424* (2013.01); *A61B 2017/00477* (2013.01); *A61B 2017/00734* (2013.01); *A61B 2017/291* (2013.01); *A61B 2017/2903* (2013.01); *A61B 2017/2905* (2013.01)

(58) Field of Classification Search
CPC .. A61B 2017/0046; A61B 2017/00477; A61B 2017/00734; A61B 2017/2905; A61B 2017/2918; A61B 34/00; A61B 2017/291; A61B 2017/2903
See application file for complete search history.

(56) References Cited

U.S. PATENT DOCUMENTS

| | | | |
|---|---|---|---|
| 6,793,653 | B2 | 9/2004 | Sanchez et al. |
| 6,902,560 | B1 | 6/2005 | Morley et al. |
| 7,338,513 | B2 | 3/2008 | Lee et al. |
| 8,002,767 | B2 | 8/2011 | Sanchez et al. |
| 8,790,243 | B2 | 7/2014 | Cooper et al. |
| 8,821,480 | B2 | 9/2014 | Burbank |
| 8,939,891 | B2 | 1/2015 | Sanchez et al. |
| 8,968,312 | B2 | 3/2015 | Marczyk et al. |
| 9,017,314 | B2 | 4/2015 | Malkowski et al. |
| 9,050,120 | B2 | 6/2015 | Swarup et al. |
| 9,119,616 | B2 | 9/2015 | Ma |
| 9,173,643 | B2 | 11/2015 | Morley et al. |
| 2003/0109857 | A1* | 6/2003 | Sanchez ............... A61B 34/37 606/1 |
| 2005/0187575 | A1* | 8/2005 | Hallbeck ............ A61B 17/2909 606/205 |
| 2007/0208375 | A1 | 9/2007 | Nishizawa et al. |
| 2008/0065116 | A1* | 3/2008 | Lee .................... A61B 17/2909 606/142 |
| 2008/0287862 | A1 | 11/2008 | Weitzner et al. |
| 2011/0112517 | A1* | 5/2011 | Peine .................... A61B 17/29 606/1 |
| 2011/0118748 | A1* | 5/2011 | Itkowitz ................ A61B 34/37 606/130 |
| 2011/0184378 | A1* | 7/2011 | Kobayashi ......... A61B 18/1477 604/500 |
| 2012/0004502 | A1* | 1/2012 | Weitzner ................ A61B 17/29 600/102 |
| 2012/0095298 | A1* | 4/2012 | Stefanchik ......... A61B 17/2909 600/219 |
| 2012/0130401 | A1* | 5/2012 | Barrier ................... A61B 34/70 606/130 |
| 2012/0143173 | A1* | 6/2012 | Steege ................... A61B 17/29 606/1 |
| 2012/0253326 | A1* | 10/2012 | Kleyman ............... A61B 34/71 606/1 |
| 2012/0277762 | A1* | 11/2012 | Lathrop ................ A61B 34/70 606/130 |
| 2013/0150833 | A1 | 6/2013 | Peine et al. |
| 2015/0080908 | A1* | 3/2015 | Lathrop ................ A61B 17/29 606/130 |

FOREIGN PATENT DOCUMENTS

| | | |
|---|---|---|
| EP | 1584300 | 10/2005 |
| WO | WO 2008/123936 | 10/2008 |
| WO | WO 2015/029041 | 3/2015 |
| WO | WO 2017/154007 | 9/2017 |

OTHER PUBLICATIONS

International Search Report and the Written Opinion dated May 31, 2017 From the International Searching Authority Re. Application No. PCT/IL2017/050307. (11 Pages).
Supplementary European Search Report and the European Search Opinion dated Sep. 6, 2019 From the European Patent Office Re. Application No. 17762651.2. (6 Pages).
Notification of Office Action and Search Report dated Jul. 1, 2020 From the State Intellectual Property Office of the People's Republic of China Re. Application No. 201780015984.2 and Its Summary in English. (12 Pages).

* cited by examiner

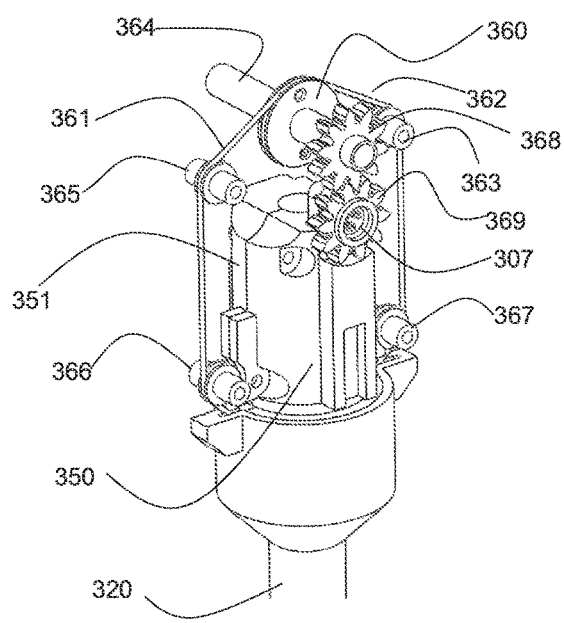
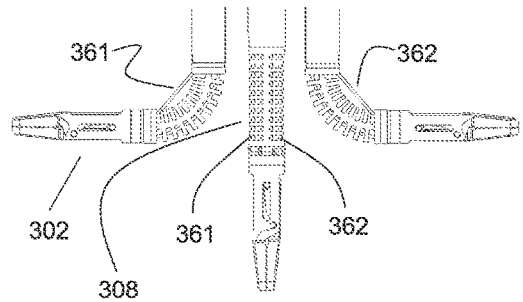
FIG. 5A
FIG. 5B

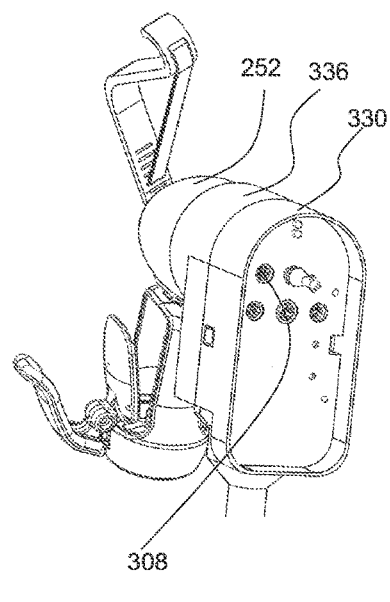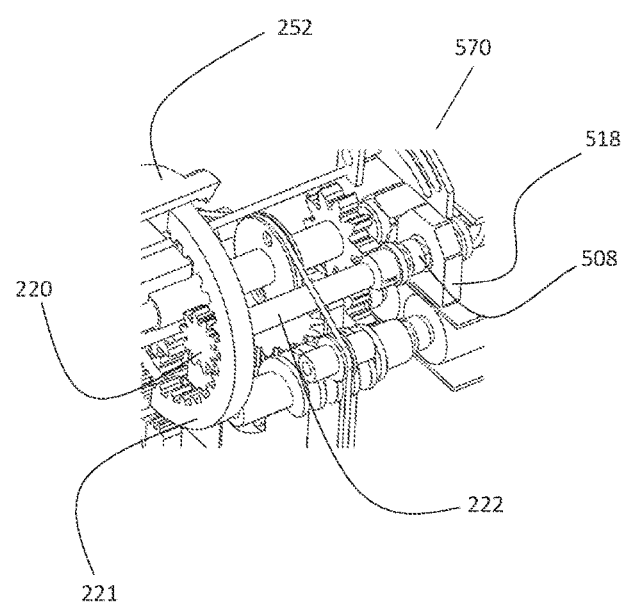
FIG. 8C
FIG. 8D

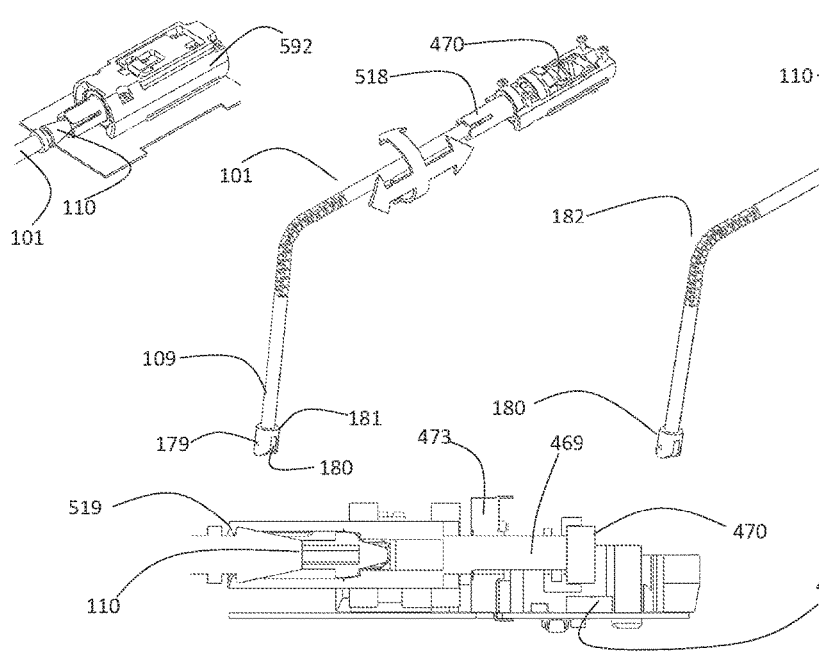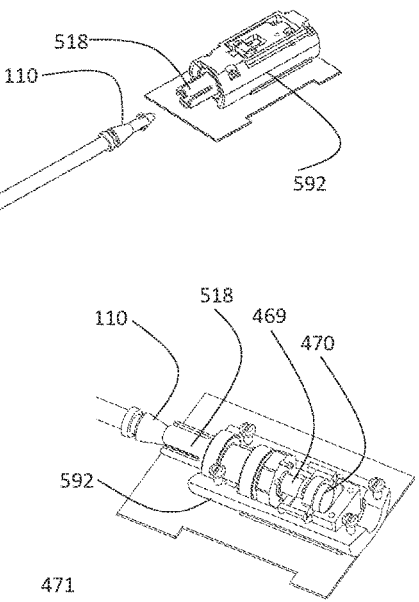

CONTROL UNIT FOR A MEDICAL DEVICE

RELATED APPLICATIONS

This application is a National Phase of PCT Patent Application No. PCT/IL2017/050307 having International filing date of Mar. 9, 2017, which claims the benefit of priority under 35 USC § 119(e) of U.S. Provisional Patent Application No. 62/306,118 filed on Mar. 10, 2016. The contents of the above applications are all incorporated by reference as if fully set forth herein in their entirety.

FIELD AND BACKGROUND OF THE INVENTION

The present invention relates to a control unit for a medical device and, more particularly, to a control unit and integrated user interface which enable translation of natural hand movements to an attached medical tool such as a laparoscopic tool to thereby enable precise and fine control over the position and function of the medical device.

Medical devices such as endoscopes and catheters are widely used in minimally invasive surgery for viewing or treating organs, cavities, passageways, and tissues. Generally, such devices include an elongated device body which is designed for delivering and positioning a distally-mounted instrument (e.g. scalpel, grasper or camera/camera lens) within a body cavity, vessel or tissue.

Since such devices are delivered through a delivery port which is positioned through a small incision made in the tissue wall (e.g. abdominal wall), and are utilized in an anatomically constrained space, it is desirable that the medical device or at least a portion thereof be steerable, or maneuverable inside the body using controls positioned outside the body (at the proximal end of the medical device). Such steering enables an operator to guide the device within the body and accurately position the distally-mounted instrument at an anatomical landmark.

Various interfaces for endoscopic instruments have been described in the prior art, see, for example, U.S. Patent Application Nos. 2008/0255420 and 2012/0041450 and U.S. Pat. No. 7,572,253.

However, there remains a need for a control unit having an interface that allows the surgeon to easily and intuitively maneuver and control an attached surgical tool.

SUMMARY OF THE INVENTION

According to one aspect of the present invention there is provided a control unit for a medical instrument, the control unit comprising: (a) a housing having a curved top surface capable of accommodating a hand of the user, the housing being attachable to the medical instrument; (b) a first interface rotatably attached to an end of the housing, the first interface being engageable by a purlicue of the hand and being for controlling a first function of the medical instrument; (c) a restraint element attached to the first interface and being capable of rotating therewith, the restraint element being for applying force to a back of the hand when positioned over the curved top surface; and (d) a second interface being attached to the first interface and being engageable by one or more fingers of the hand, the second interface being for operating at least a second function of the medical instrument.

According to further features in preferred embodiments of the invention described below, the control unit further comprising a drive unit.

According to still further features in the described preferred embodiments the drive unit is detachable from the housing.

According to still further features in the described preferred embodiments the drive unit includes at least one motor and a power source for enabling the first interface and the second interface to separately operate the medical instrument.

According to still further features in the described preferred embodiments the second interface includes levers simultaneously operable via thumb and index finger of the hand.

According to still further features in the described preferred embodiments the medical instrument is an articulating laparoscope having a grasper and further wherein the first interface controls articulation of the laparoscope.

According to still further features in the described preferred embodiments the second interface controls the grasper.

According to still further features in the described preferred embodiments the second interface controls opening and closing and rotation of the grasper.

According to still further features in the described preferred embodiments the control unit further comprising a user-engageable switch for activating/deactivating the first interface and/or the second interface.

According to another aspect of the present invention there is provided medical device comprising: (a) a control unit including: (i) a housing having a curved top surface capable of accommodating a hand of the user; (ii) a first interface rotatably attached to an end of the housing, the first interface being engageable by a purlicue of the hand; (iii) a restraint element attached to the first interface and being capable of rotating therewith, the restraint element being for applying force to a back of the hand when positioned over the curved top surface; and (iv) a second interface being attached to the first interface and being engageable by one or more fingers of the hand; and (b) a medical instrument attached to the housing and being operable via the first interface and the second interface.

According to still further features in the described preferred embodiments the medical device further comprising a drive unit.

According to still further features in the described preferred embodiments the drive unit is detachable from the housing.

According to still further features in the described preferred embodiments the drive unit includes at least one motor and a power source.

According to still further features in the described preferred embodiments the at least one motor engages a drive interface for the medical instrument when the drive unit is attached to the housing.

According to still further features in the described preferred embodiments the drive unit electrically communicates with the first interface and the second interface when the drive unit is attached to the housing.

According to still further features in the described preferred embodiments the second interface includes levers simultaneously operable via thumb and index finger of the hand.

According to still further features in the described preferred embodiments the medical instrument is an articulating laparoscope having a grasper and further wherein the first interface controls articulation of the laparoscope.

According to still further features in the described preferred embodiments the second interface controls the grasper.

According to still further features in the described preferred embodiments the second interface controls opening and closing and rotation of the grasper.

According to still further features in the described preferred embodiments the medical device further comprising a user-engageable switch for activating/deactivating the first interface and/or the second interface.

The present invention successfully addresses the shortcomings of the presently known configurations by providing a control unit for a medical instrument. The control unit includes a user interface that enables a user to simultaneously control the movement and actuation of, for example, a laparoscope using a single hand.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a general view of the control unit; FIG. 1B illustrates the regions of a surgeon's hand (palm side) that interface with the control unit. FIGS. 1C-D illustrate the control unit with detached drive unit and sterile cover (shown detached from drive unit in FIG. 1C and attached over the drive unit in FIG. 1D).

FIGS. 5A-C illustrate the control unit mechanism (FIGS. 5A-C) for articulating the shaft of a medical instrument (FIG. 5B).

FIGS. 8A-D illustrate the articulation mechanism of the purlicue interface of the present control unit.

FIGS. 10A-E illustrate in detail the fingers actuatable mechanism of the drive unit.

DESCRIPTION OF THE PREFERRED EMBODIMENTS

Figure 1A:
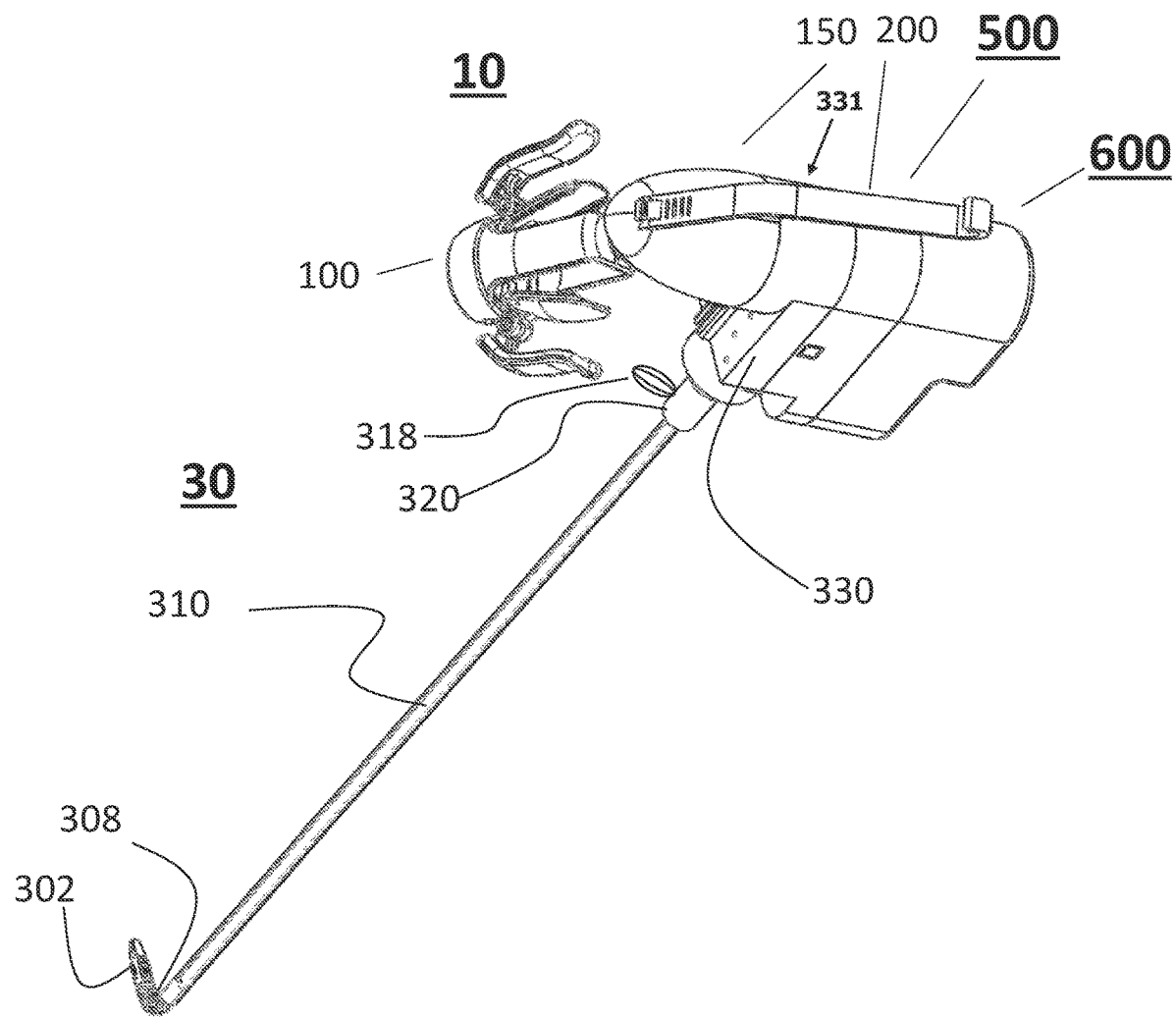
FIGS. 1A-D illustrate one embodiment of the control unit of the present invention attached to a medical instrument (laparoscope shown).

The present invention is of a control unit which can be used to maneuver and operate an attached medical instrument. The control unit includes an interface which can be used to control the movement, position and function of an attached medical instrument such as a laparoscope.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In laparoscopic surgery, a surgeon has to position the distal end portion (including a tissue manipulating end, e.g., grasper) of a medical instrument such as a laparoscope within a body cavity (e.g. abdominal cavity) and adjacent to treated tissue. In order to correctly position the laparoscope, the surgeon has to spatially orient the entire laparoscope while controlling deflection of the steerable portion and actuating the tissue manipulating end.

A surgeon typically uses an interface (graspable handle and lever) of a surgical tool for positioning, maneuvering, holding and operating the device and effector end at the tissue site of interest. While presently used device interfaces can provide such functionality, they can be limited by a tradeoff between maneuverability and operability of the entire device and its effector end (instrument mounted on a distal end of a laparoscope shaft) or limited by a steep learning curve thus requiring considerable time and effort on the part of the surgeon to complete a minimally invasive treatment procedure.

Experiments conducted by the present inventors demonstrated that an interface that provides single hand control over all of the functions of a medical instrument such as a laparoscope is typically difficult to master due to the complexity of movements and the number of interfaces. The present inventors set out to design a single hand control unit that is easy to master and provides the functions most needed by surgeons. As is further describes hereinunder, the present inventors devised a miniature, light weight motorized control unit with intuitive interfaces that enable a surgeon to easily maneuver and operate an attached medical instrument such as a laparoscope using a single hand.

Thus, according to one aspect of the present invention there is provided a control unit for a medical instrument.

As used herein, the phrase "medical instrument" refers to any instrument used in an internal or external procedure (e.g. surgery). The medical instrument can be a laparoscope fitted with a grasping tool, cutting tool and the like, an endoscope fitted with a camera and/or delivery/suction channels or a catheter, cannula and the like.

The user interface of the present invention is particularly suitable for use with a laparoscope having a steerable (deflectable) distal portion and a distally-mounted instrument such as a grasper or cutter.

Laparoscopes are widely used in minimally invasive surgery for viewing or treating organs, cavities, passageways, and tissues. Generally, such devices include an elongated device body which is designed for delivering and positioning a distally-mounted instrument (e.g. scalpel, grasper or camera/camera lens) within a body cavity, vessel or tissue.

Since such devices are delivered though a delivery port which is positioned through a small incision made in the tissue wall (e.g. abdominal wall), and are utilized in an anatomically constrained space (within, for example, the abdominal cavity), it is desirable that the medical device or at least a portion thereof be steerable, or maneuverable inside the body using controls positioned outside the body (at the proximal end of the medical device). Such steering enables an operator to guide the device within the body and accurately position the distally-mounted instrument at an anatomical landmark.

Numerous examples of steerable devices are known in the art, see for example, U.S. Pat. Nos. 2,498,692; 4,753,223; 6,126,649; 5,873,842; 7,481,793; 6,817,974; 7,682,307 and U.S. Patent Application Publication No. 20090259141.

Deflection of the steerable portion is typically effected via one or more control wires which run along the shaft of the device to the distal end of the steerable portion.

The proximal end of each control wire can be connected to the control unit such that pulling of the wire bends the device shaft and deflects the steerable portion with relation to the pulled wire.

The device effector end (distally-mounted instrument) is controlled via one or more additional wires which are similarly connected to the control unit and actuated by the user interface. Thus, the control unit of a steerable device such as a steerable laparoscope provides three separate functions, positioning of the device shaft with respect to the tissue access site (up/down right/left in/out, angle) deflection of the steerable portion, and actuation of the distally mounted instrument in the case of grasper, open/close and rotation of the jaws.

The control unit of the present invention includes a housing having a curved top surface for accommodating a portion of the palm of a hand of the user. The housing contains electronic circuitry for transferring user control actions to a drive unit and a drive mechanism (gears, levers, shafts, wires, belts etc) for transferring a driving force from the drive unit to an attached medical instrument.

The electronic circuitry translates in real time (via a microcontroller) the hand/finger movements of the surgeon to commands for motors/actuators of the drive unit. The motors/actuators then drive the attached medical instrument functions through the drive mechanism.

The control unit further includes a first interface which is rotatably attached to an end of the housing (also referred to herein as the 'front end'). The first interface is engageable by a purlicue of the hand (the palm-side cleft between the thumb and index finger) and is designed for controlling a first function of the medical instrument.

The control unit optionally further includes a restraint element which is attached to the first interface such that it rotates therewith. The restraint element is designed for applying a force to a back of the hand when the hand is positioned over the curved top surface of the housing.

The control unit further includes a second interface which is attached to the first interface. The second interface is engageable by one or more fingers of the hand (e.g. thumb and index finger) and is designed for operating at least a second function of the medical instrument.

The user interface of the present control unit provides single hand control over an attached medical instrument in the following manner:

(i) the shaft of the medical device can be moved in and out, up and down and side to side with respect to, for example, a tissue access site via hand and arm movement (primarily by flexing/extending the wrist and elbow joints and rotating the shoulder joint);

(ii) a steerable portion of the shaft can be deflected by tilting (rotating side to side) the first interface (primarily by rotating the wrist join); and (iii) a distally mounted tissue manipulating end can be actuated (open/close and rotation) via finger movement (primarily about the inter-phalangeal joints and the meta-carpal-phalangeal joints).

The present control unit provides several advantages when used to position and operate a medical instrument such as a steerable laparoscope:

(i) greater and more natural maneuverability—a laparoscope can be operated using less effort and without requiring extreme maneuvering of body and limbs;

(ii) simultaneous control over three functions—laparoscope spatial positioning, shaft steering and effector end actuation;

(iii) single hand operation—all movements are controlled via a single hand using three interface regions, the palm/dorsum, purlicue and fingers;

(iv) compact and intuitive interface with instinctive operational controls that are easy to master; and (v) can be used to control any attached/integrated medical instrument.

Referring now to the drawings, FIG. 1A illustrates the present control unit which is referred to herein as control unit 10.

Figure 1B:
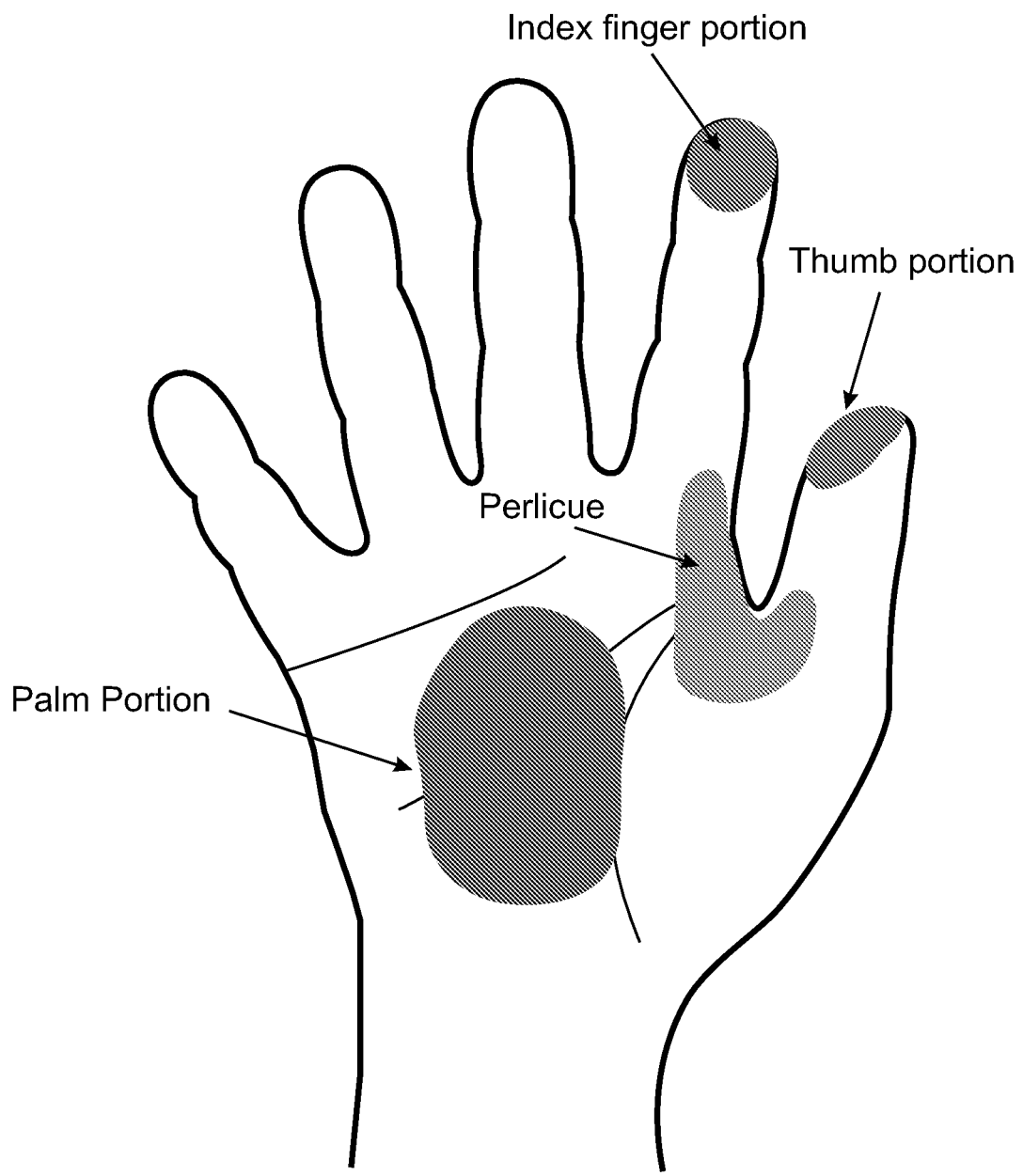

FIG. 1A illustrate control unit 10 having housing 330 with a curved top surface 331 designed for accommodating a palm portion of a hand (shown in FIG. 1B). A medical instrument 30 is shown attached to housing 330 via coupler 320 positioned at a bottom side of housing 330. Medical instrument 30 can include diathermia functions provided from electrical plug 318.

Housing 330 (and interfaces 100 and 150 described below) can be fabricated from a polymer and/or alloy using machining, 3D printing and/or casting/molding fabrication approaches. Housing 330 can be 10-40 mm wide, 10-40 mm deep and about 60-100 mm in height. Curved top portion 331 can have a radius of curvature of 10-60 mm.

First interface 150 (also referred to herein as interface 150) is rotatably attached to a front end of housing 330 and is capable of tilting side to side. Interface 150 is designed to be engaged by a purlicue of a hand (shown in FIG. 1B) such that rotation of the wrist joint side to side tilts first interface through an arc of 60-120 degrees. A dorsum retaining element 200 is attached to first interface 150 and rotates therewith and is designed for restraining the palm portion against curved top surface 331 of housing 330.

Tilting of interface 150 to one side results in corresponding deflection of articulation 308 of medical instrument 30 (laparoscope shaft 310 shown with grasper 302). Control unit 10 can be designed such that the degree of deflection of articulation 308 can directly correspond to the degree of tilting of first interface 150 or to increase/decrease the degree of deflection with respect to the degree of tilting.

Control unit 10 further includes second interface 100 (also referred to herein as interface 100) which is engageable by a thumb and index finger portions of a user (shown in FIG. 1B). Interface 100 is attached to interface 150 and rotates therewith. Interface 100 can actuate tissue effector end such as grasper 302 to open and close by opening and closing the thumb and index finger.

Control unit 10 includes a drive mechanism which is attachable to control wires running the length of shaft 310 of medical device 30. The drive mechanism actuates the wires that in turn actuate shaft deflection and grasper opening closing and rotation.

The drive mechanism can be manually driven (e.g. directly connected to interfaces 100 and 150 via levers) or it can be driven by a drive unit 500 removably attachable to housing 330. Drive unit 500 includes a motor/actuator and power source (battery) and can be reused by fitting a sterilizable cover 600 around it. Housing 330, interfaces 100 and 150 as well as attached medical instrument 30 can be disposable.

Cover 600 (FIG. 1C) is fabricated from a sterilizable elastic material such as PC, ABS, PC/ABS and/or Thermoset photo polymer. Once sterilized, cover 600 is carefully fitted over drive unit 500 without allowing drive unit 500 to contact external surfaces of cover 600. The covered drive unit 500 is then coupled to housing 330 of control unit 10 and cover 600 is secured to housing 300 via releasable connectors such as snaps, buttons, hooks or the like. Cover 600 isolates the exposed parts of drive unit 500 from the environment allowing safe use in the operating room without fear of contamination.

To disassemble control unit 10, a user simply releases the connectors allowing cover 600 and drive unit 500 to be removed from housing 330. Drive unit 500 can then be removed from cover 600 and be reused with another sterile cover in another procedure.

Figure 1C:
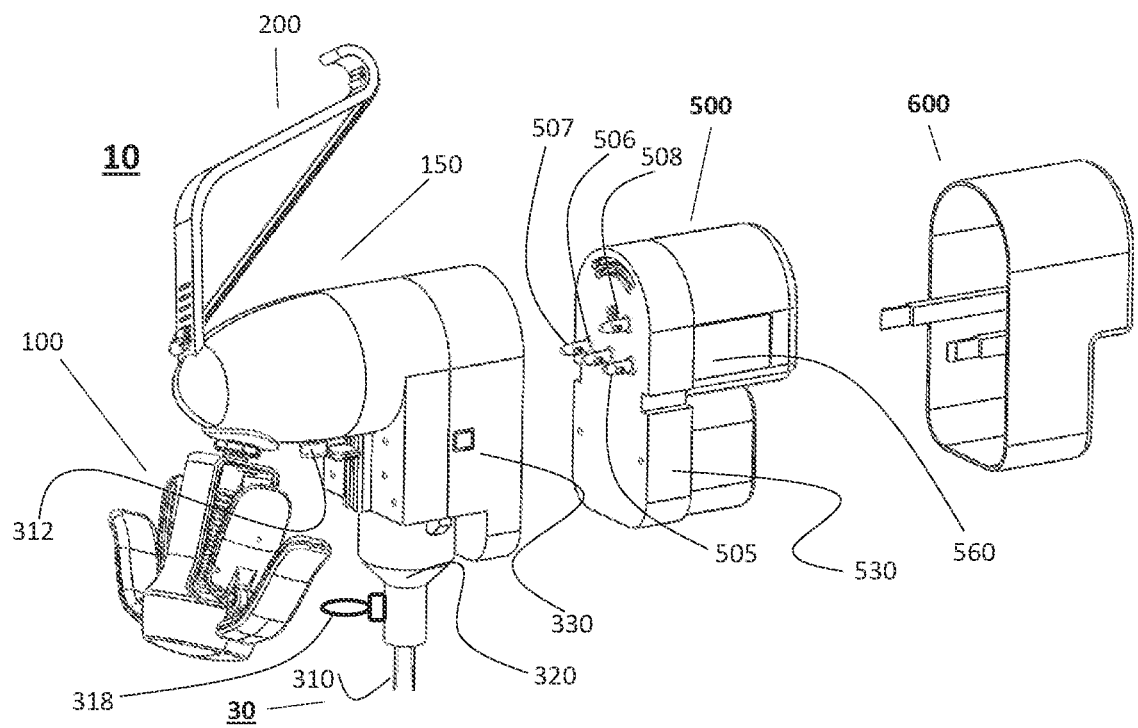

FIG. 1C illustrates housing 330, interfaces 100 and 150 and detached drive unit 500 and sterile cover 600.

Drive unit 500 can include a motor pack, a control unit composed mainly of electrical circuits, a battery pack and optional screen, speaker and buttons for user control and feedback. The shaft(s) of the motor pack engages drive ends 505, 506, 507 which protrude out of housing 530.

Figure 1D:
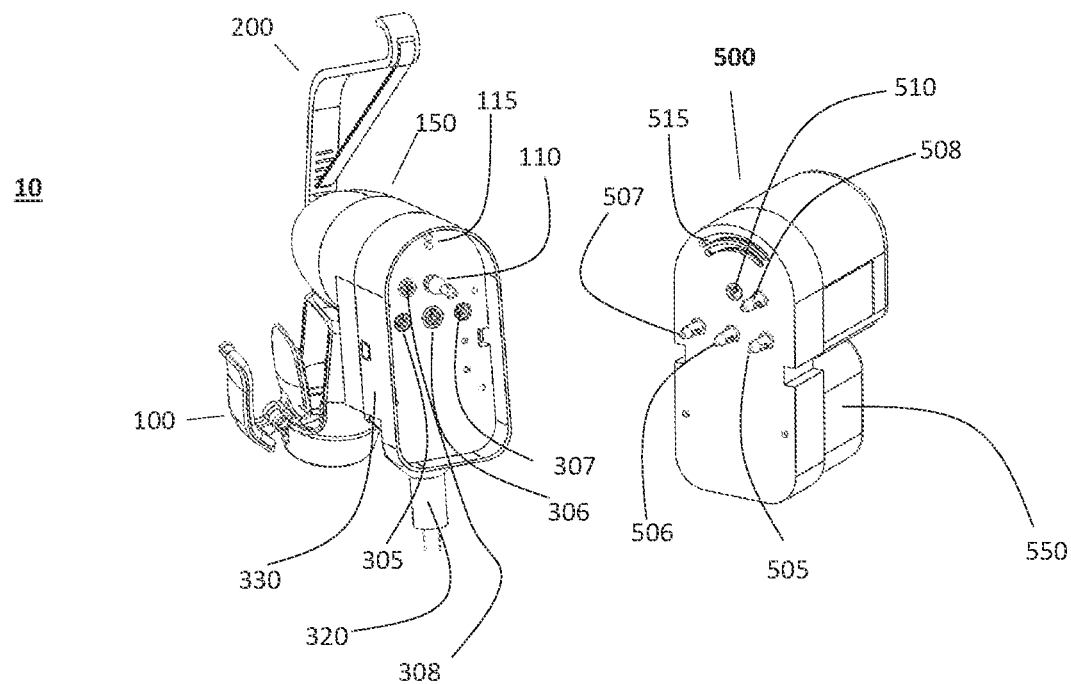

FIG. 1D illustrates the mechanical interface between housing 330 and drive unit 500. Sockets 305, 306, 307, which form a part of a drive mechanism of housing 330, are shown at the rear face of housing 330. Drive shaft ends 505, 506, 507 protruding out of housing 530 of the drive unit 500 engage sockets 305, 306, 307 of the drive mechanism when drive unit 500 is coupled to housing 330.

Shaft 110 of the flexible drive shaft of finger interface mechanism, engages socket 510 of drive unit 500. Shaft 110 is connected to finger interface 100 and transfers movement at finger interface 100 (i.e. open/close and rotation) to sensors of a control unit of drive unit 500 for operating the motor pack. When drive unit 500 is connected to housing 330, electrical contacts 115 and 515 of the drive unit 500 transmit signals from mode button 312 (shown in FIG. 1C) to drive unit 500.

Figure 2A:
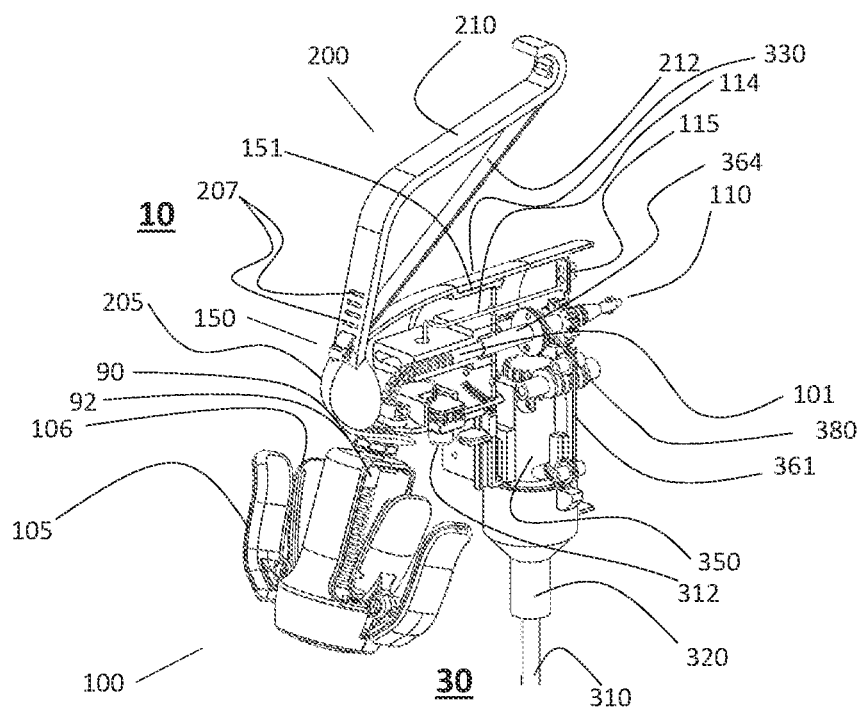
FIGS. 2A-B illustrate the internal drive mechanism of the control unit of the present invention.

FIG. 2A illustrates the drive mechanism within lumen 350 of housing 330. Interface 100 is connected to a front end of interface 150 via tube 92 and nut 90. Flexible shaft 101 is connected at its front end to interface 100 and runs through tube 92 and tube 364 at the rear side of the drive mechanism. Shaft head 110 is connected to flexible shaft 101. Cables 361, 362 and pulley 360 rotate with shaft 364, resulting in deflection of a steerable portion of a shaft of an attached medical device.

Restraining element 200 is connected at the front of interface 150 via a pivoting connector 205. Interface 150 is connected to housing 330 via rotating surface 151. Electric mode button 312 is placed at the bottom of interface 150 with wiring 114 connecting button 312 to contacts 115.

Figure 2B:
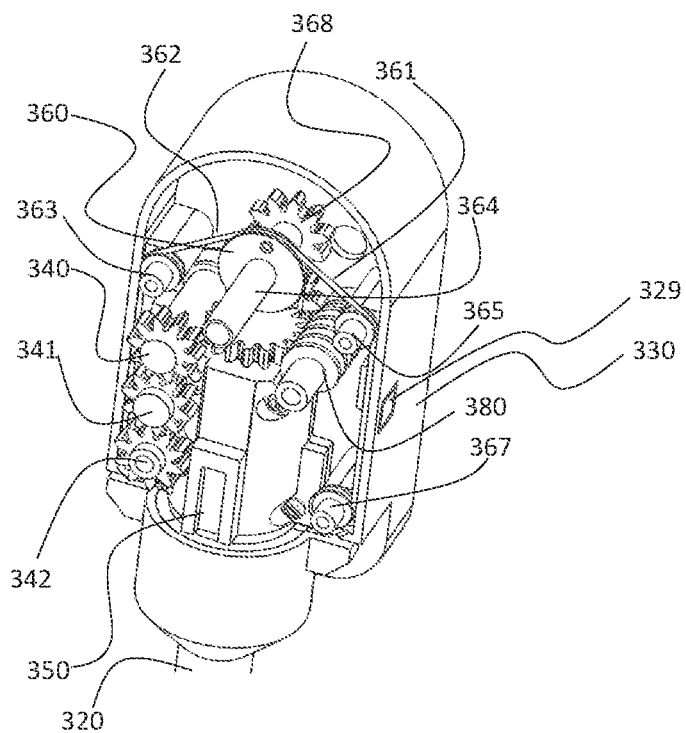

FIG. 2B illustrate the drive mechanisms for articulating a steerable shaft and actuating a grasper.

At the top of housing 330, hollow shaft 364 is fixed to pulley 360 and gear 368 and cable 361 is routed over pulleys 365 and 367. Coupler 320 connects housing 330 to shaft 310 of medical instrument 30 (not shown). Gears 340-342 transmit rotation from one motor socket of drive unit 500 to a jaw rotation mechanism, while worm gear 380 transmits rotational movement from another motor socket to a jaw open/close mechanism. Lever 329 secures sterile cover 600 when drive unit 500 is coupled to housing 330.

Figures 3A, 3B, 3C:
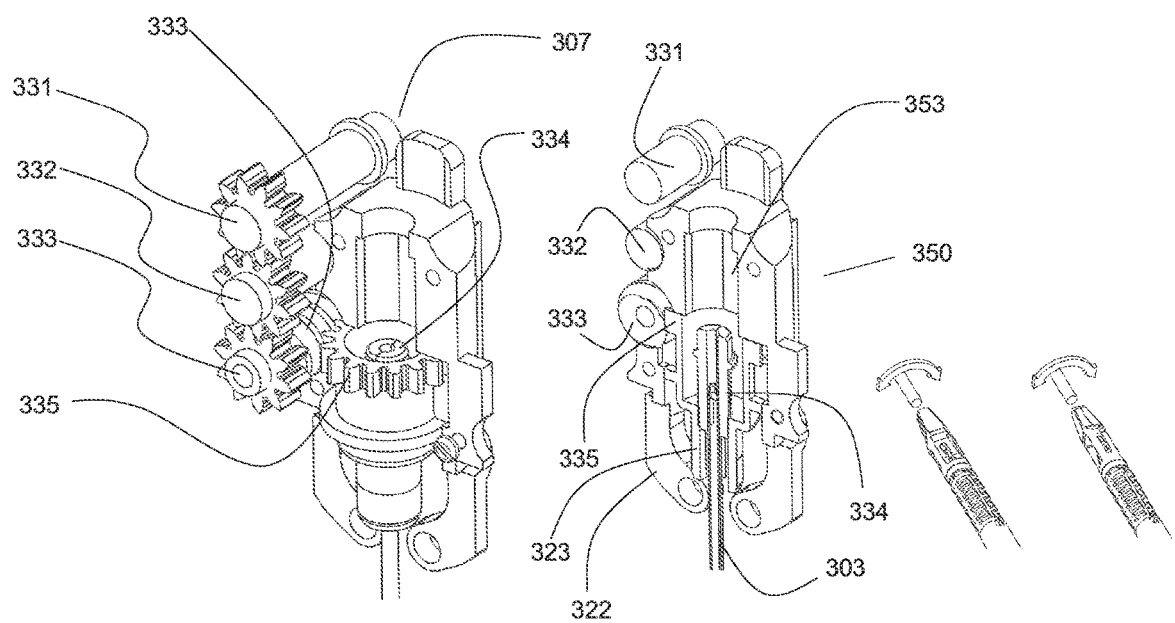
FIGS. 3A-C illustrate the control unit mechanism (FIGS. 3A-B) for rotating the effector end of the medical instrument (FIG. 3C).
Figure 4A:
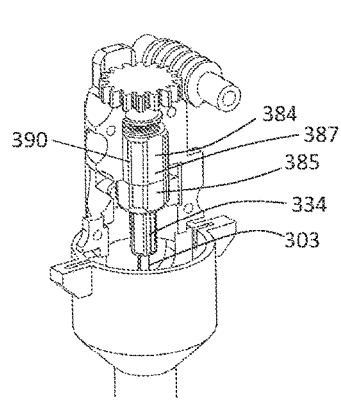
FIGS. 4A-E, illustrate the control unit mechanism (FIGS. 4A-D) for opening and closing a grasper effector end (FIG. 4E).
Figure 4B:
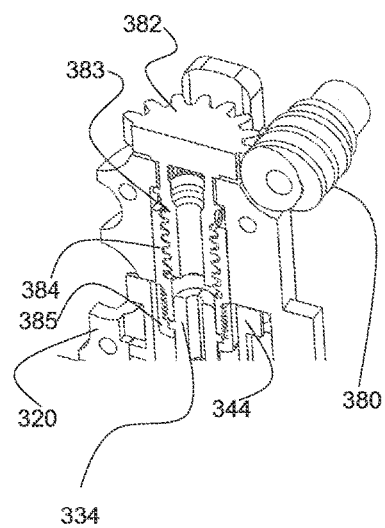
Figure 4C:
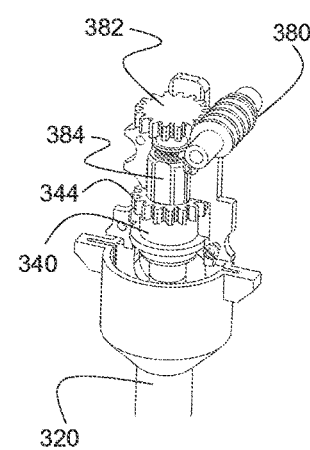
Figures 4D, 4E:
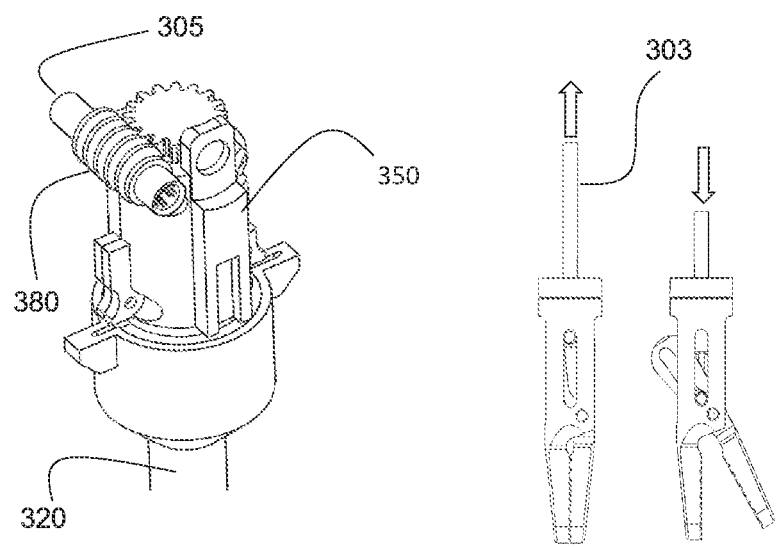

FIGS. 3A-C illustrate in details the jaws rotation mechanism. Hexa-shaped nut 334 is fixed to shaft 303. The hexa-shaped nut 334 slides freely up and down through opening 323 of gear 335 which is located at the bottom end of housing 350; rotation of gear 335 rotates hexa-shaped nut 334.

Gear 335 is rotated by worm gear 333 which is in turn rotated by spur gears 331, 332, 333. Spur gear 333 and worm gear 335 are fixed onto the same shaft and rotate together; when shaft 303 rotates, jaws rotate as shown in FIG. 3C.

FIGS. 4A-E illustrate in details the mechanism for actuating opening and closing of the jaws of medical device 30 grasper 302. Hexa clamp 390 holds hexa nut 334 between upper part 384 and lower part 385. At the clamping area between part 384 and 385 nut 334 is round and can rotate with respect to hexa clamp 390, while allowing clamp 390 to move nut 334 forward and backward. Part 384 has an internal thread for accepting screw 383 which is fixed to gear 382; rotation of gear 382 rotates screw 383. Parts 384 and 385 have flat surfaces (identical to surface 387). Portion 350 of housing 330 has internal flat surfaces 353 (shown in FIG. 3B) that match the flats surfaces of clamp 390. These sliding flat surfaces 353 of housing 350 and 387 of clamp 390 do not allow clamp 390 to rotate. Thus, when screw 384 is rotated clamp 390 move back and forth according to direction of the rotation. When clamp 390 moves forward and backward it moves shaft 303 (FIG. 4E) resulting in opening/closing movement of the jaws.

FIGS. 5A-B illustrate in detail the pulley mechanism that articulates region 308 (FIG. 1A) of shaft 310.

Gear 369 rotates gear 368 which is fixed to shaft 364. Pulley 360 is also fixed to shaft 364 such that when gear 368 rotates, shaft 364 rotates along with pulley 360. Cables 361, 362 are connected to pulley 360, thus when pulley 360 is rotated to one direction one cable is pulled and the other cable is released, resulting in deflection of element 308 (FIG. 5B).

Figure 5C:
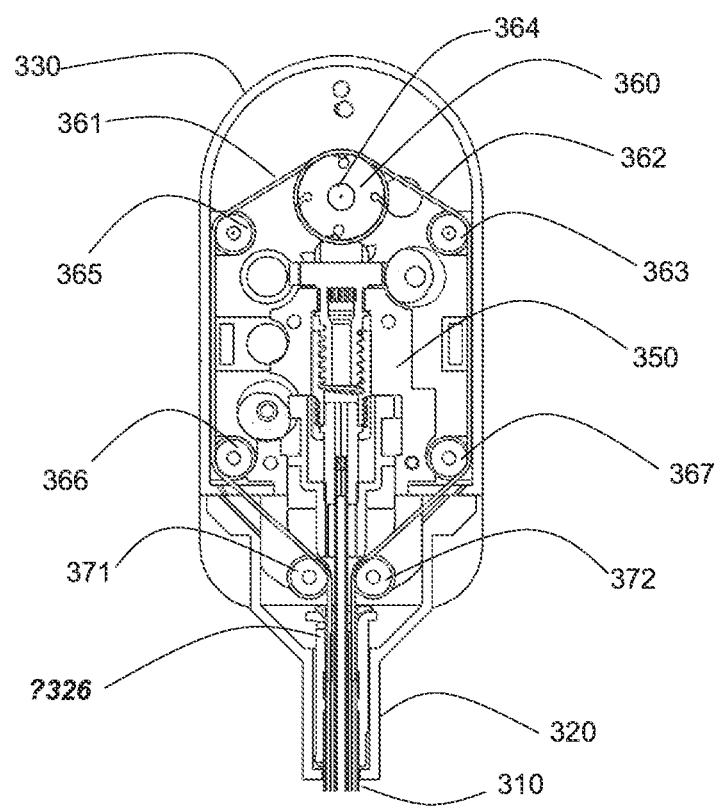

FIG. 5C illustrates routing of cables 361 and 362 from articulation pulley 360 through routing pulleys 363, 367 and pulley 372 into opening 326 of shaft 310.

Figures 6A, 6B, 6C, 6D:
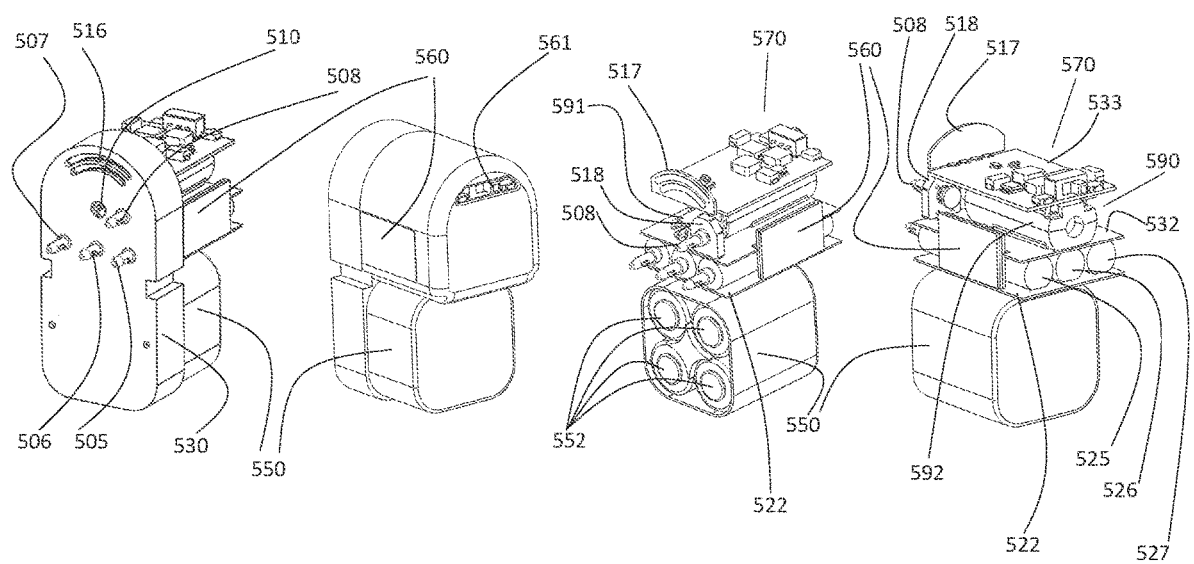
FIGS. 6A-D illustrate the detachable drive unit of the control unit of the present invention.

FIGS. 6A-D illustrate in detail drive unit 500 of control unit 10. FIG. 6A is a front view of drive unit 500 showing drive shaft ends 505, 506, 507 and rotation sensor head 508 protruding out of housing 530 of the drive unit 500. Rotation sensor head 508 engages gear head 308 located at interface 150 to measure the rotation (tilt angle) of interface 150. Socket 591 of sensors 590 engage interface 100 enabling measurement of finger movements. Touch screen 560 of drive unit 500 (located on the side of housing 530) allows the user to get information about drive unit 500 mode of operation and battery status and to verify drive setting (speed etc) inputted by the user.

Figure 7A:
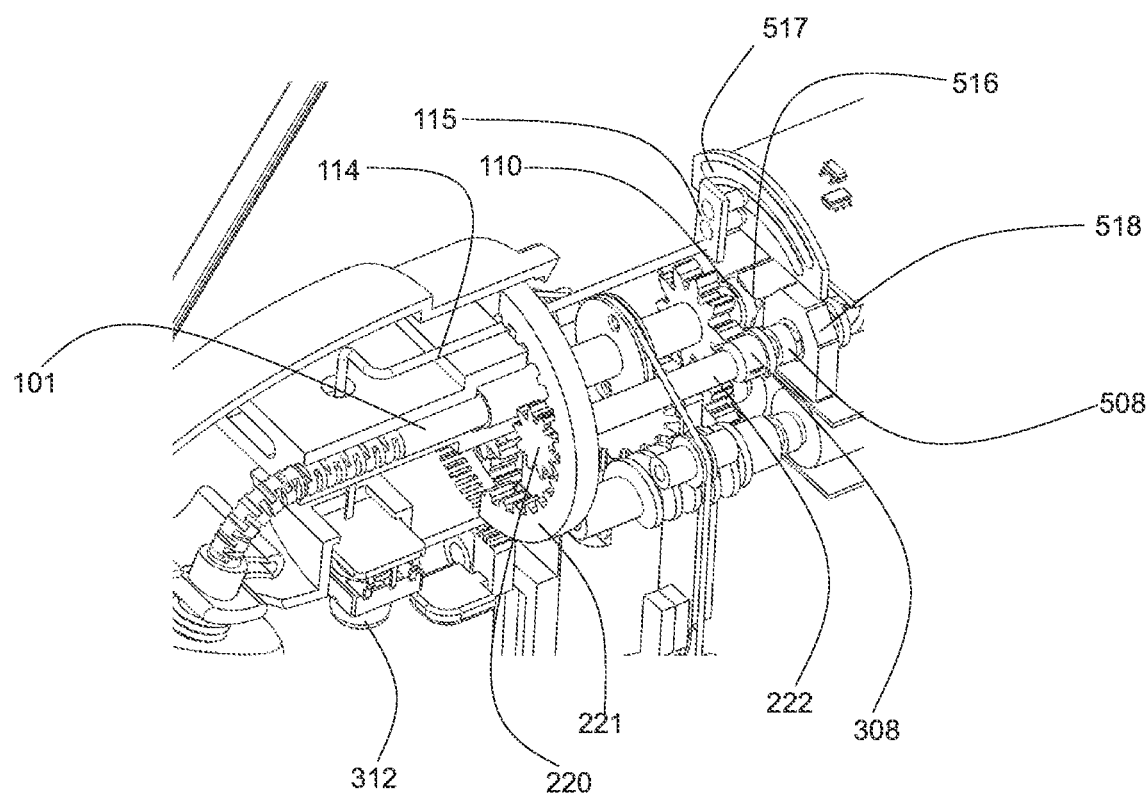
FIGS. 7A-B illustrate the mechanical linkage between the drive unit, medical instrument and interfaces of the control unit of the present invention.
Figure 7B:
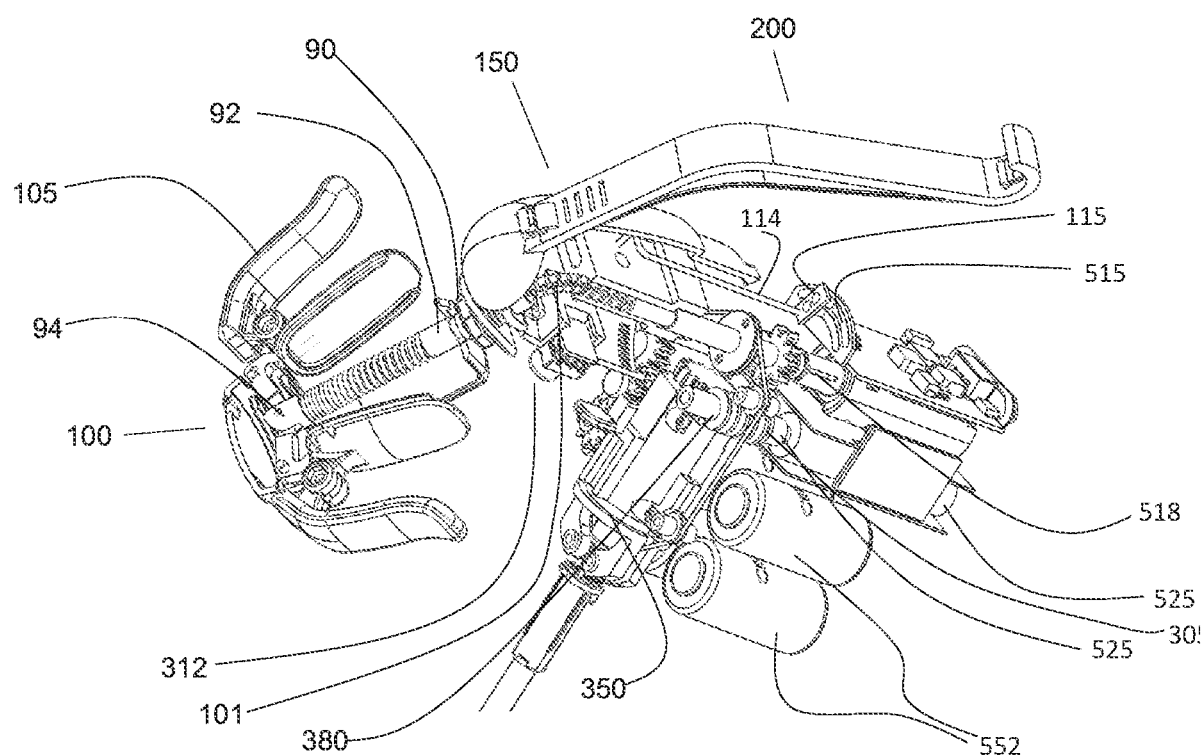

FIG. 6B shows the rear side of drive unit 500 with on/off switch 561. FIGS. 6C-D show front and rear views of the internal components of drive unit 500. A battery pack 552 is located at the bottom of drive unit housing 530. Battery pack 552 can include, for example, 4 CR123 type batteries arranged in 2 layers in battery pack housing 550. Motors 525, 526, 527 (DC, brushless or steps type) are located on top of battery pack 552 and are connected to motors driver circuits (PCB) 522. Control unit 570 is located above the motors unit and a sensor unit 590 is located between PCB's 532 and 533 which contain the electrical circuits for receiving and processing sensors signals (from interfaces and motors) to generate motor commend signals. PCB's 532 and 533 also include touchscreen and wireless communication components. PCB 517 contains 2 arced shape contacts that engage with contacts 115 of the interface. FIGS. 7A-B illustrate the interface between control unit 10, medical instrument 30 and drive unit 500. A portion of medical instrument 30, housing 330 of the surgical tool, and a portion of interface 150 and housing 530 have been removed from these figures for clarity purposes. Interface 100 mechanically transfer finger opening/closing movement via flexible shaft 101 and interface 150 is purlicue-actuated rotational (tilt side to side) movement. Gear 220 is coupled to gear 221 which is fixed to interface 150 and thus, rotation of interface 150 rotates gear 221. Gear 220 is fixed to shaft 222 and rotates with gear 222. A socket 308 located at the distal end of shaft 222 can be engaged to rotate sensor head 508 of rotation sensor 518 with shaft 222.

When the user tilts interface 150 (with purlicue motion), a scaled rotation movement is transferred to rotation sensor 518. The signals from rotation sensor 518 are processed by the control unit of drive unit 500 into motor operation.

Figure 8A:
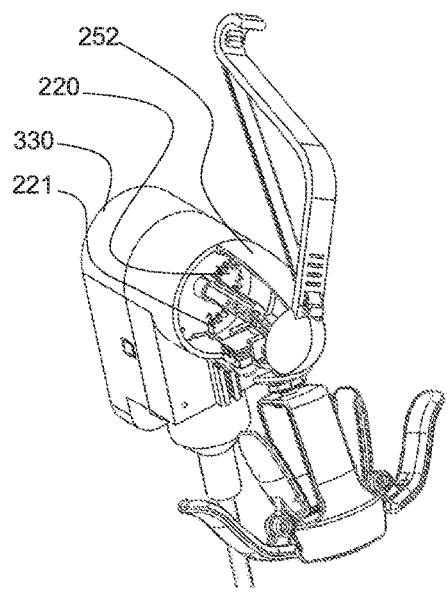
Figure 8B:
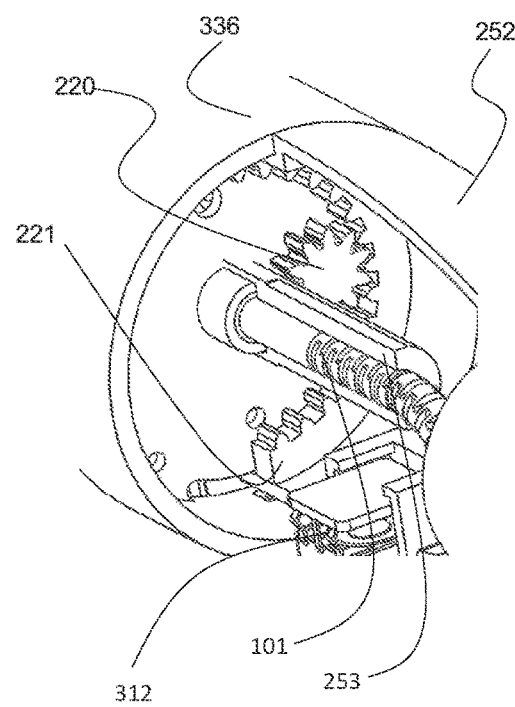

FIGS. 8A-C illustrate in more details the tilt measuring mechanism of interface 150. Gear 220 is coupled to gear 221 which is fixed to interface 150 via inner part of holding surface 252. Tilting of interface 150 by the purlicue of a user's hand rotates gear 221 which transfers rotation to gear 220 (which is rotationally connected to housing 330) to rotates shaft 222 (shown in FIGS. 8A-B). Interface 150 also includes central tube 253 of flexible shaft 101 that transfers interface 100 movements to control unit 570 located in housing 530.

FIG. 8D is a cut-away view of interface 150 showing the mechanism that transfers rotation of interface 150 through gear 221 (that rotates with interface 150) to rotation sensor 518 of control unit 570. When the user tilts interface 150, a scaled rotation movement is transferred to rotation sensor 518; the signals from rotation sensor 518 are processed by the control unit into operation of the motor of drive unit 500.

Figures 9A, 9B:
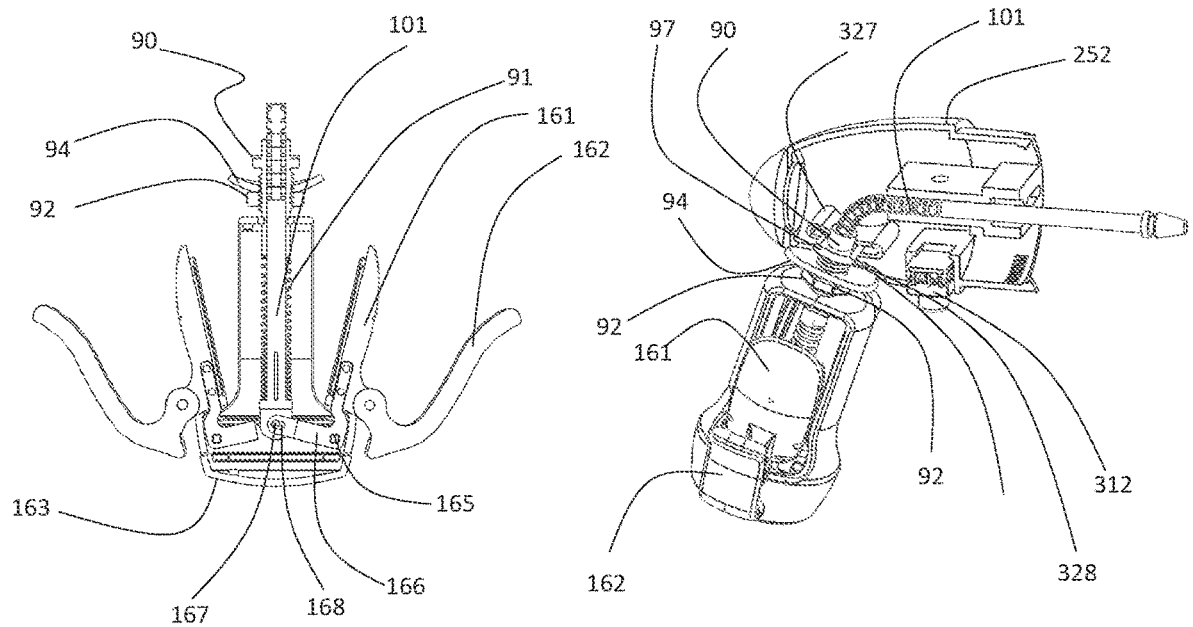
FIGS. 9A-D illustrate the finger interface of the present control unit.

FIGS. 9A-D illustrate finger interface 100 of control unit 10. FIGS. 9A-B illustrates shaft 90 and nut 92 which connect interface 100 to interface 150. In order to use interface 100 simultaneously with interface 150, the user places the purlicue of a hand on interface 150 and a thumb and index finger on levers 161. Optional external wings 162 may be used to secure the thumb and index finger within levers 161. The angle between a lever 161 and a wing 162 can be adjusted via hinge 164.

To close jaws of tool 302, a user closes levers 161; releasing levers 161 enables spring 91 to open levers 161 thereby opening jaws 302; rotating housing 163 around shaft 90 rotates jaws 302.

Figure 9C:
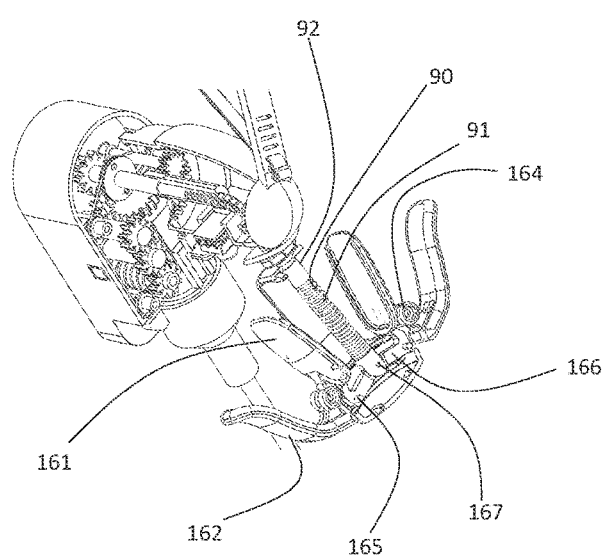
Figure 9D:
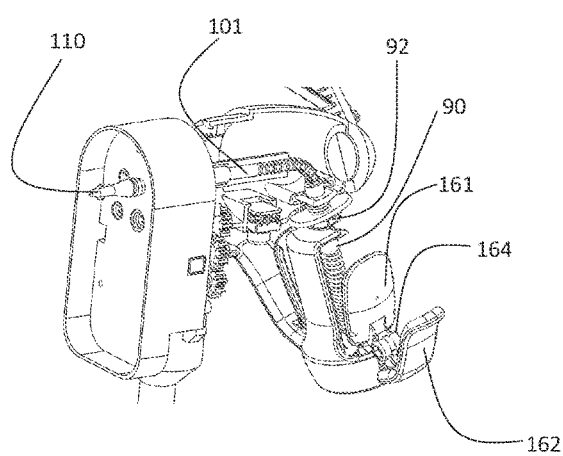

FIGS. 9C-D illustrate the internal mechanism of interface 100. Inner levers 161 are fixed to brackets 166 which rotate around hinge 165. Pin 169 of central shaft 101 is positioned through elongated holes 167 at the end of brackets 166. Rotation of brackets 166 by inner levers 161 leads to linear movement of shaft 101 (through pin 167). Spring 91 located on straight part 109 of shaft 101 between distal part of shaft 90 and the distal end 181 of shaft 10, is stretched when the user applies a closing force on levers 161. When this closing force is released spring 91 contracts linearly and shaft 101 returns to its original position.

FIGS. 10A-E illustrate the connection between flexible shaft 101 operated by interface 100 and the movement sensors of control unit 592 of drive unit 500. A magnet 470 is fixed to the end of flexible shaft 101 (FIGS. 10A-B). Connector 518 and a magnetic sensor 471 (FIG. 10E) are positioned parallel to the main plane of shaft 469 (FIGS. 10D-E). Sensor 471 which measures the linear movement of magnet 470 is sampled by control unit of drive unit 500 which is used to control the open-close movement and position of the jaws via motor.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following example, which together with the above descriptions, illustrate the invention in a non limiting fashion.

Interface Design Based on Manual Object-Picking Patterns

In a previously filed patent application (WO2015029041), Applicant disclosed a motorized articulated surgical tool having a user interface capable of measuring the orientation of a user's palm in three axis relative to the interface housing. Orientation measurements were translated into electrical signals and processed into command signals for actuating articulation of a medical device shaft and operation of an effector end thereof.

Following numerous studies conducted with the aforementioned user interface, the present inventors observed that while the interface of WO2015029041 was highly efficient in controlling an attached medical device, the learning period required to master this interface was relatively long for inexperienced users.

Figure 11A:
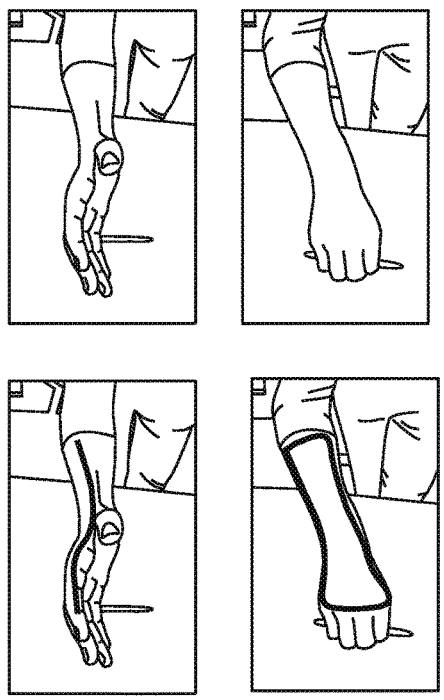
FIGS. 11A-C illustrate a prototype constructed in accordance with the teachings of the present invention.

In order to substantially decrease the time required to master an interface for a surgical device, the present inventors studied users tasked with picking objects from a surface in an effort to decipher the patterns of movements used for such activity. A pencil was placed on a table surface and each subject in the study was instructed to place a hand over a pencil and pick it up as quickly as possible when hearing an audio signal. Of the 15 subjects tested, all demonstrated the pattern of picking up the pencil shown in FIG. 11A.

In order to pick the pencil the tested subjects rotated their palm to an orientation which is parallel to the table surface (left images) thus enabling their thumb and index finger to quickly clamp over the pencil (right images).

The results of this study indicated that in order to shorten the time needed to master control over a medical device, the user interface of the device must orient the user's hand such that the plane of the hand is perpendicular to the shaft of a medical instrument attached to the user interface and not allow the palm to roll or pitch with respect to the interface housing.

The lessons learned from this study were used to develop a user interface that measures purlicue and finger movements while restricting the palm of the user from moving with respect to the interface housing.

Figure 11B:
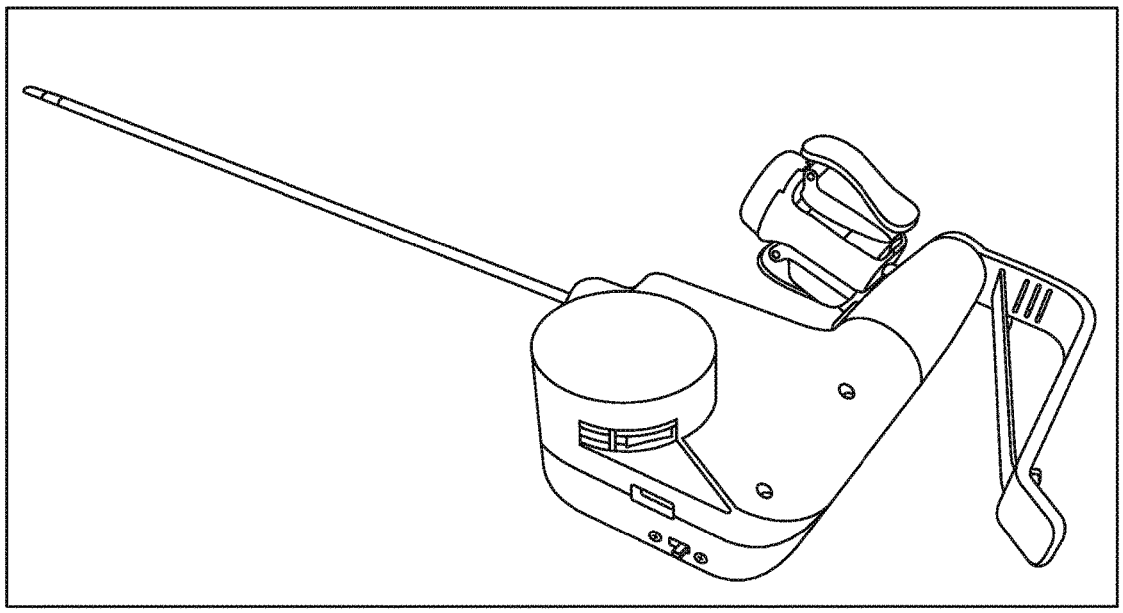
Figure 11C:
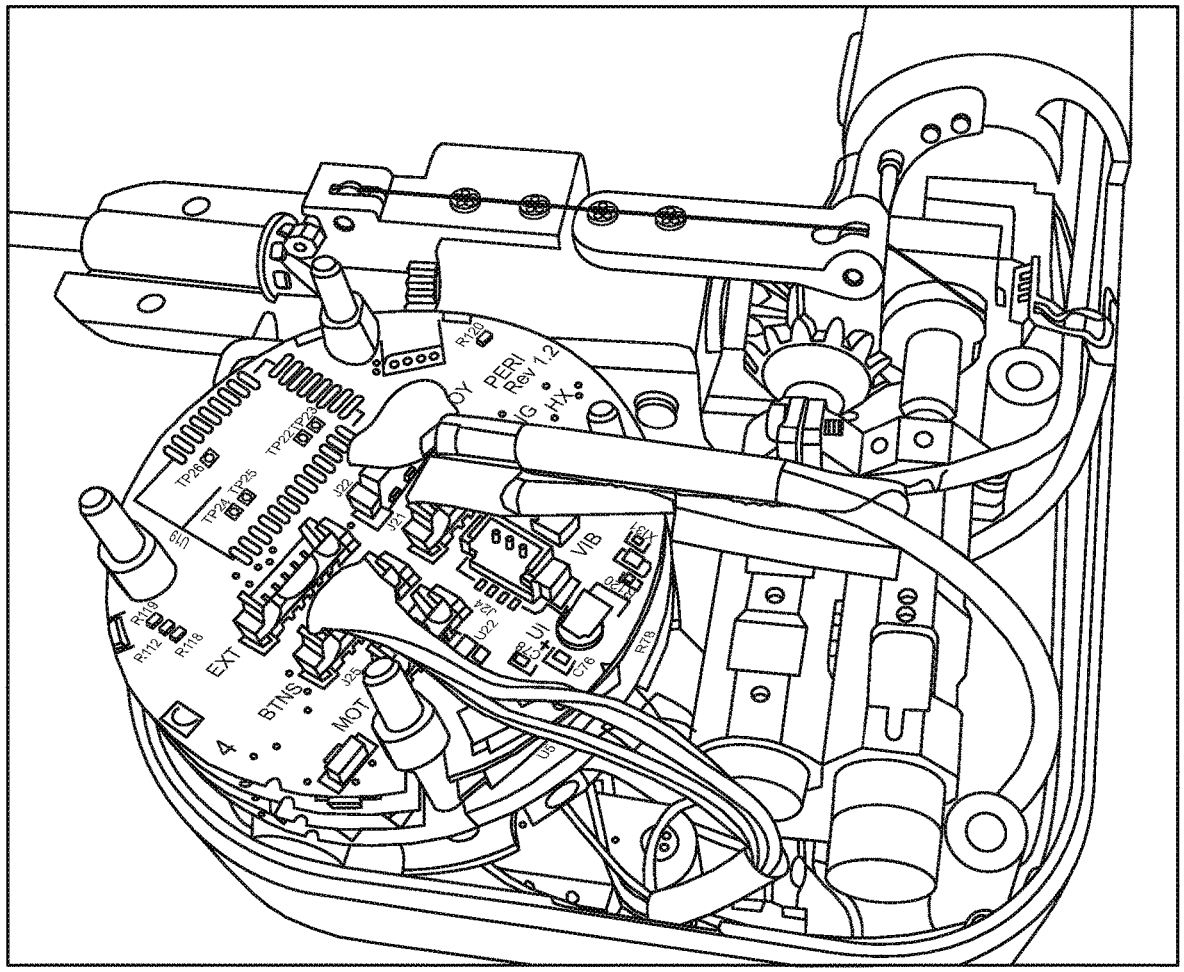

A prototype medical device (FIGS. 11B-C) was developed and tested on a group of users who were instructed to use the interface controls (first and second interfaces described hereinabove) in order to pickup objects from a table surface.

This test showed that eliminating palm movements with respect to the interface housing considerably shortened the time needed to achieve full control over device shaft articulation and effector end operation. Interestingly, following a time period of using this new interface, users adapted quicker to operating more complex interfaces such as the one described in WO2015029041.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A control unit for a medical instrument, the control unit comprising:
   (a) a housing having a curved top surface forming a palm rest engageable by a palm of a hand, said palm rest being immovable with respect to said housing and said housing being attachable to the medical instrument;
   (b) a first interface rotatably attached to an end of said housing, said first interface being engageable by a purlicue of said hand and being for controlling a first function of the medical instrument;
   (c) a restraint element attached to said first interface and being capable of rotating therewith, said restraint element being for applying force to a back of said hand when positioned over said curved top surface; and
   (d) a second interface being attached to said first interface and being engageable by one or more fingers of said hand, said second interface being for operating at least a second function of the medical instrument.

2. The control unit of claim 1, further comprising a drive unit.

3. The control unit of claim 2, wherein said drive unit is detachable from said housing.

4. The control unit of claim 3, wherein said drive unit includes at least one motor and a power source for enabling said first interface and said second interface to separately operate the medical instrument.

5. The control unit of claim 1, wherein said second interface includes levers simultaneously operable via thumb and index finger of said hand.

6. The control unit of claim 1, wherein said second interface can be tilted with respect to said first interface.

7. The control unit of claim 1, wherein the medical instrument is an articulating laparoscope having a grasper and further wherein said first interface controls articulation of said laparoscope.

8. The control unit of claim 7, wherein said second interface controls said grasper.

9. The control unit of claim 7, wherein said second interface controls opening and closing and rotation of said grasper.

10. The control unit of claim 1, further comprising a user-engageable switch for activating/deactivating said first interface and/or said second interface.

11. A medical device comprising:
    (a) a control unit including:
    (i) a housing having a curved top surface forming a palm rest engageable by a palm of a hand, said palm rest being immovable with respect to said housing;
    (ii) a first interface rotatably attached to an end of said housing, said first interface being engageable by a purlicue of said hand;
    (iii) a restraint element attached to said first interface and being capable of rotating therewith, said restraint element being for applying force to a back of said hand when positioned over said curved top surface;
    (iv) a second interface being attached to said first interface and being engageable by one or more fingers of said hand; and
    (b) a medical instrument attached to said housing and being operable via said first interface and said second interface.

12. The medical device of claim 11, further comprising a drive unit.

13. The medical device of claim 12, wherein said drive unit is detachable from said housing.

14. The medical device of claim 13, wherein said drive unit includes at least one motor and a power source.

15. The medical device of claim 14, wherein said at least one motor engages a drive interface for said medical instrument when said drive unit is attached to said housing.

16. The medical device of claim 14, wherein said drive unit electrically communicates with said first interface and said second interface when said drive unit is attached to said housing.

17. The medical device of claim 11, wherein said second interface includes levers simultaneously operable via thumb and index finger of said hand.

18. The medical device of claim 11, wherein said medical instrument is an articulating laparoscope having a grasper and further wherein said first interface controls articulation of said laparoscope.

19. The medical device of claim 18, wherein said second interface controls said grasper.

20. The medical device of claim 18, wherein said second interface controls opening and closing and rotation of said grasper.

21. The medical device of claim 11, further comprising a user-engageable switch for activating/deactivating said first interface and/or said second interface.

* * * * *

UNITED STATES PATENT AND TRADEMARK OFFICE
CERTIFICATE OF CORRECTION

PATENT NO. : 10,993,734 B2
APPLICATION NO. : 16/081044
DATED : May 4, 2021
INVENTOR(S) : Mordehai Sholev et al.

It is certified that error appears in the above-identified patent and that said Letters Patent is hereby corrected as shown below:

On the Title Page

Item (73) Assignee:
"Hsiman Extensions Ltd."
Should be changed to:
-- Human Extensions Ltd. --

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*